United States Patent [19]

Weisrock

[11] 4,311,796

[45] Jan. 19, 1982

[54] METHOD FOR IMPROVING SPECIFIC XANTHAN PRODUCTIVITY DURING CONTINUOUS FERMENTATION

[75] Inventor: William P. Weisrock, Tulsa, Okla.

[73] Assignee: Standard Oil Company (Indiana), Chicago, Ill.

[21] Appl. No.: 168,884

[22] Filed: Jul. 14, 1980

[51] Int. Cl.³ .............................................. C12P 19/06
[52] U.S. Cl. .................................. 435/104; 435/813; 435/910
[58] Field of Search ....................... 435/104, 813, 910

[56] References Cited

U.S. PATENT DOCUMENTS 3,328,262 6/1967 Lindblom et al. .................. 435/104
3,485,719 12/1969 Rogovin .............................. 435/104

FOREIGN PATENT DOCUMENTS 7612448 5/1977 Netherlands .
1512536 1/1978 United Kingdom .
2008138 5/1979 United Kingdom .

OTHER PUBLICATIONS

Davidson, FEMS Microbiology Letters, vol. 3, pp. 347-349.
Silman et al., Biotechnology and Bioengineering, vol. XIV, pp. 23-31 (1972).
Silman et al., Biotechnology and Bioengineering, vol. XII, pp. 75-83 (1970).

Primary Examiner—Lionel M. Shapiro
Attorney, Agent, or Firm—F. E. Hook; W. E. Murray; A. McIlroy

[57] ABSTRACT

In the production of xanthan gum by the action of Xanthomonas bacteria on a nutrient medium, the specific productivity of the organism employed can be improved by the increase in average cell concentration through the stepwise increase of growth limiting nutrients in the medium.

16 Claims, No Drawings

METHOD FOR IMPROVING SPECIFIC XANTHAN PRODUCTIVITY DURING CONTINUOUS FERMENTATION

INTRODUCTION

The present invention relates to a method for improving the efficiency of the process for producing heteropolysaccharides, such as xanthan gum, by the action of bacteria of the genus Xanthomonas on suitable nutrient media. More particularly, it is concerned with improvement of the specific productivity of Xanthomonas species during continuous fermentation. The expression "specific productivity", for the purpose of the present description is a measurement of the amount of product formed by a given quantity of cells in a given unit of time, e.g., generally expressed as gm of product/gm cells/hr.

BACKGROUND OF THE INVENTION

Fermentation of the inoculated medium with Xanthomonas organisms for 36-72 hours under aerobic conditions, results in the formation of xanthan gum which is separated from other components of the medium by precipitation with acetone or methanol in a known manner. Because of the time required to ferment each batch, the low bipolymer content of the fermented medium and the processing steps required for the recovery and purification of the product, xanthan is relatively expensive.

Earlier work has indicated that the heteropolysaccharides produced by the action of Xanthomonas bacteria on carbohydrate media have potential application as film forming agents, as thickeners for body building agents in edible products, cosmetic preparations, pharmaceutical vehicles, oil field drilling fluids, fracturing liquids, and emulsifying, stabilizing, and sizing agents. Heteropolysaccharides, particularly xanthan gum, have significant potential as mobility control agents in micellar polymer flooding. Xanthan gum has excellent viscosifying properties at low concentration, it is resistant to shear degradation and exhibits only minimal losses in viscosity as a function of temperature, pH, and ionic strength. For these reasons, it is an attractive alternative synthetic polyacrylamides for enhanced oil recovery operations.

However, in order for xanthan gum to be used in enhanced oil recovery operations as a mobility control agent, the cost must be sufficiently low to make such operations economical. The economics of xanthan production by continuous fermentation are more favorable than when a batch fermentation process is employed. It has been shown that the economics of continuous xanthan fermentation are sensitive, at least in part, to the specific productivity at which the culture is operating. Therefore, any process improvements which enhance specific productivity will improve the overall economics. For example, at a dilution rate of 0.08 hr $^{-1}$, increasing the specific productivity from 0.12 to 0.2 gm xanthan/gm cells/hr can lower the per pound price of xanthan by as much as 20%.

The most pertinent prior art of which I am aware is as follows:

1. P. Rogovin, et al., 1970, "Continuous Fermentation to Produce Xanthan Biopolymers: Laboratory Investigation", Biotechnol. Bioeng., XII, pp. 75-83.

2. K. W. Silman, et al., 1972, "Continuous Fermentation to Produce Xanthan Biopolymer: Effect of Dilution Rate", Biotechnol. Bioeng., XIV, pp. 23-31.

3. P. Rogovin, et al., U.S. 3,485,719, "Continuous Production of Xanthan".

4. G. P. Lindblom, et al., U.S. Pat. No. 3,328,262, "Heteropolysaccharide Fermentation Process".

5. Netherlands Patent Application No. 7,612,448, "Method for the Production of Bacterial Polysaccharides".

6. "Production of Polysaccharides by *Xanthomonas campestris* in Continuous Culture", FEMS Microbiology Letters, 347-349 (1978) by I. W. Davidson.

7. "Process for the Production of Xanthan Gum", British Patent Application No. 2,008,138 (A. Tate and Lyle, LTD).

SUMMARY OF THE INVENTION

During continuous culture, the concentration of biomass is set by the concentration of the limiting nutrient being fed with the medium and biomass concentration can be varied by raising or lowering the limiting nutrient concentration. Ordinarily when biomass concentration is varied one would not expect that the specific productivity or xanthan production efficiency of the culture would be changed. In other words, if cell concentration is doubled, xanthan concentration in the output should also double since all cells in the culture should continue to make xanthan at the same rate. If one were to expect any change in specific productivity to occur, it would be toward a decreased specific productivity because as xanthan concentration increases, viscosity also increases and this could lead to problems of mass transfer of nutrients into the cell and the transport of xanthan away from the cell, thus, lowering production efficiency.

Contrary to the foregoing, I have found that by growing a species of the genus Xanthomonas for example, *Xanthomonas campestris*, in continuous culture in a medium containing glucose, mineral salts, and NH$_4$Cl and either glutamate or glutamate plus yeast extract, the specific productivity can be improved by first operating (under nitrogen-limited conditions) at a cell concentration of about 2 gm/liter and then raising the cell concentration up to 4-5 grams/liter. Where mentioned throughout the present description and claims, the cell concentration is given in terms of dry weight. The increase in cell concentration is obtained by increasing the concentration of nitrogen, the limiting nutrient in the medium. Of course, other elements in place of nitrogen as the limiting nutrient, such as, for example, phosphorous, sulfur or potassium, may be employed. The amount of limiting nutrient may vary from about 0.1 to 15%, preferably 0.3 to 10% of the desired cell concentration at steady state although concentration levels of from about 0.001 to about 0.07% are useful. Where nitrogen is the limiting nutrient it can be supplied by NH$_4$Cl, glutamate, yeast autolysate, yeast extract or various combinations thereof.

The continuous culture process used is standard from the standpoint of equipment and environmental conditions employed. Any continuous fermenter configuration may be used with provisions for medium input, culture harvesting, agitation, aeration, temperature and pH control, foam control and measurement of dissolved oxygen.

After seeding the medium with an inoculum of culture (usually 5 to 10% of the medium volume), the culture is allowed to grow in a batch mode for 24 to 48 hours until a desired cell concentration is reached. The medium employed contains glucose, mineral salts, and ammonium chloride, with or without glutamic acid, as well as either a mixture of vitamins or vitamins plus glutamic acid, or glutamic acid plus yeast extract. Other amino acids may be substituted for glutamic acid such as L-histidine, methionine, tryptophan, tryrosine, threonine, aspartic acid, asparagine, and arginine. Yeast autolysate may be substituted for or combined with yeast extract as a nitrogen source.

Continuous culture is initiated by pumping in fresh sterile medium at a desired flow rate and drawing off product at the same rate, based on an overflow level control device. The dilution rate (flow rate divided by fermenter liquid volume) is set to be initially 75% of the maximum specified growth rate of the culture. After two culture turnovers (a turnover is the time required to completely replace 1 volume of broth in the fermentation vessel, or the reciprocal of the dilution rate), the dilution rate is set at the desired level.

Initially the cell concentration is set in a range of 1.5 to 2.5 gm/liter. After steady state has been reached in the culture, the cell concentration is increased to approximately double by addition of more nitrogen to the input medium, again in the form of ammonium chloride, glutamate, or yeast extract. Steady state occurs when culture parameters which are not externally controlled, such as xanthan productivity, xanthan concentration, and residual glucose, are essentially constant. The cell concentration should be increased after at least about three culture turnovers and after preferably about ten culture turnovers. Once cell concentration increases and a new steady state reached, the specific productivity is found to be higher than during the original steady state at lower cell concentration.

In carrying out the process of the present invention, the following broad and preferred operating conditions are noted below:

| | |
|---|---|
| Dilution Rate | 0.01–0.14 hr$^{-1}$ |
| Preferably | 0.04–0.1 hr$^{-1}$ |
| Temperature: | 20–35° C. |
| Preferably | 25–35° C. |
| pH: | 5.5–8.5 |
| Preferably | 6.0–7.4 |
| Air Rate: | 0.2–2 vvm |
| Preferably | 0.5–1 vvm |
| Agitation Rate: | 200–1200 rpm |
| Preferably | 500–800 rpm |
| Dissolved O$_2$: | 5–90% of saturation |
| Preferably | 20–80% of saturation |

The expression "nutrient medium" as used in the present description and claims is intended to mean a medium that contains in known composition and proportions, essential mineral salts, trace elements, glucose or equivalent carbohydrate, and defined supplemental organic growth factors; i.e., vitamins with or without appropriate amino acids such as those name above. In place of the defined nitrogen source, an undefined source thereof such as yeast extract, yeast autolysate, etc., may be employed. Representative species of the Xanthomonas genus which may be used in carrying out my invention include *Xanthomonas carotae*, *Xanthomonas phaseoli*, *Xanthomonas papaverilcola*, *Xanthomonas begoniae*, *Xanthomonas hederae*, *Xanthomonas translucens*, *Xanthomonas vasculorum*, *Xanthomonas vesicatoria*, *Xanthomonas incanae*, and *Xanthomonas malvacearum*.

Cultures of these organisms as well as other of this genus may be obtained from the American Type Collection in Rockville, Maryland.

SPECIFIC EMBODIMENTS OF THE INVENTION

The present invention will be further illustrated by the following specific examples:

EXAMPLE I

*Xamthomonas campestris* NRRL B-1459 was grown continuously in a 7.5 liter fermenter using a liquid nutrient medium having the following composition:

| Ingredient | Amt/Liter |
|---|---|
| Dextrose | 22.5 gm |
| L-Histidine | 1 mg |
| DL-Methionine | 2 mg |
| L-Tryptophan | 2 mg |
| Biotin | 2 mcg |
| Ca Pantothenate | 400 mcg |
| Folic Acid | 3000 mcg |
| Inositol | 2000 mcg |
| Niacin | 400 mcg |
| p-Amino Benzoic Acid | 200 mg |
| Pyridoxine HCl | 200 mcg |
| Riboflavin | 200 mcg |
| Thiamine Hcl | 400 mcg |
| H$_3$BO$_3$ | 500 mcg |
| CuSO$_4$ | 40 mcg |
| KI | 100 mcg |
| FeCl$_3$ | 3.98 mg |
| MnSO$_4$ | 400 mcg |
| Na$_2$MoO$_4$ | 200 mcg |
| ZnSO$_4$ | 400 mcg |
| KH$_2$PO$_4$ | 1 gm |
| KgSO$_4$ | 0.5 gm |
| KCl | 0.57 gm |
| NaCl | 0.1 gm |
| CaCl$_2$ | 0.1 gm |
| NH$_4$Cl | 0.37 gm |
| Citric Acid | 0.11 gm |

The culture was operated initially for 84 hours at a dilution rate of 0.053 hr$^{-1}$. The nitrogen was supplied by ammonium chloride at a nitrogen concentration of 0.036%. This gave an average cell concentration of 2.87 gm/liter resulting in a specific productivity of 0.15 gm/gm cells/hr (ranging between 0.13 and 0.17). After raising the dilution to 0.104 hr$^{-1}$, the culture was operated for 49 hours at an average cell concentration of 2.53 gm/liter, and the specific productivity decreased to an average of 0.13 gm/gm cells/hr. Next the concentration of nutrients in the medium was increased to 1.5 strength, but the nitrogen concentration was kept constant at 0.035% at a dilution rate of 0.106 hr$^{-1}$. The unit was operated in this mode for 74 hrs. The average cell concentration was 2.13 gm/liter and specific productivity was 0.14 gm/gm cells/hr. Thus, increasing the concentration of inorganic nutrients and vitamins but not nitrogen had no effect on specific productivity.

Next glutamic acid was incorporated into the medium, everything else being kept constant such that the total nitrogen concentration was increased to 0.056%. This required the addition of 0.21% glutamic acid. Over the next 63 hours (279–342 hrs), the culture approached a new steady state. The cell concentration rose from 2.13 to 4.2 gm/liter and the specific productivity increased from 0.13–0.14 to 0.17–0.18 gm/gm cells/hr. When steady state was reached, the culture was maintained for 55 hours at a cell concentration of 4.36 gm/liter and an average specific productivity of 0.18

(ranging from 0.168 to 0.192 gm/gm cell/hr). Thereafter, the medium was changed to eliminate vitamins completely and resulted in the composition given below:

| Minimal Medium + Glutamic Acid | |
|---|---|
| Ingredient | Amt/Liter |
| Dextrose | 22.5 gm |
| KH₂PO₄ | 0.88 gm |
| K₂SO₄ | 0.54 gm |
| MgSO₄ 7H₂O | 0.056 gm |
| MgSO₄ 7H₂O | 0.056 gm |
| CaCl₂ 2H₂O | 0.17 gm |
| Citric acid | 0.17 gm |
| Glutamic acid | 2.07 gm |
| NH₄Cl | 1.53 gm |
| FeSO₄ 7H₂O | 16.7 mg |
| ZnSO₄ | 0.48 mg as Zn |
| MnSO₄ | 0.45 mg as Mn |
| CuSO₄ | 0.048 mg as Cu |
| Na₂MoO₄ | 0.30 mg as Mo |
| KI | 0.24 mg as I |

The nitrogen concentration was maintained at 0.055%. Over the next 88 hours, cell concentration was at an average of 4.26 gm/liter, with an average specific productivity of 0.18 (ranging from 0.169 to 0.198). During the last 77 hours of operation under the same conditions, the average cell concentration decreased slightly to 3.8 gm/liter. The specific productivity averaged 0.19 gm/gm cell/hr (ranging from 0.187 to 0.206).

Thus, from the foregoing example, it is seen that one can increase the specific productivity of a species of the genus Xanthomonas in continuous fermentation to produce xanthan gum by increasing cell concentration using ammonium chloride as the nitrogen source and supplementing with glutamic acid nitrogen. The results of the above run are noted in the table below:

TABLE I

| Time Period (Hour) | Cell Conc'n (gm/liter) | Xanthan (conc'n %) | Visc. (cp) | Xanthan Spec. Prod. (gm/gm cells/hr) | Dilution Rate (hr⁻¹) |
|---|---|---|---|---|---|
| Nutrient concentration in medium (1×); N = 0.036% | | | | | |
| 0–96 | 2.87 | 0.80 | 2950 | 0.15 | 0.053 |
| Increased dilution rate to 0.104 hr⁻¹ | | | | | |
| 96–146 | 2.53 | 0.40 | 330 | 0.13 | 0.104 |
| Nutrient concentration in medium (1.5×); N = 0.056% | | | | | |
| 146–240 | 2.13 | 0.28 | 300 | 0.14 | 0.106 |
| Medium containing glutamic acid; N = 0.056% | | | | | |
| 240–287 | Approaching steady state | | | | |
| 287–336 | 4.36 | 0.75 | 1956 | 0.18 | 0.106 |
| Removed vitamins; N = 0.055% | | | | | |
| 336–453 | 4.26 | 0.73 | 1890 | 0.18 | 0.104 |
| 453–501 | 3.8 | 0.68 | 1670 | 0.19 | 0.103 |

EXAMPLE II

*Xanthomonas campestris* NRRL B-12074, obtainable from the Northern Regional Research Center of the U.S. Department of Agriculture, Peoria, Ill., was grown in continuous culture in a medium containing glucose, mineral salts, ammonium chloride, yeast extract, and sodium glutamate. The composition of this medium is given below:

| Ingredient | Amt/Liter |
|---|---|
| NH₄Cl | 0.857 gm |
| KH₂PO₄ | 0.68 gm |
| K₂SO₄ | 0.174 gm |

| Ingredient | Amt/Liter |
|---|---|
| MgSO₄ | 0.06 gm |
| CaCl₂ | 0.011 gm |
| Yeast Extract (Difco) | 0.4 gm |
| Na glutamate | 0.02 gm |
| Citric acid | 0.09 gm |
| FeSO₄ 7H₂O | 5.56 mg |
| ZnSO₄ | 0.16 mg as Zn |
| MnSO₄ | 0.15 mg as Mn |
| CuSO₄ | 0.16 mg as Cu |
| Na₂MoO₄ | 0.1 mg as Mo |
| KI | 0.8 mg as I |
| H₃BO₃ | 0.03 mg as B |
| CoCl₂ | 0.06 mg as Co |
| Glucose | 20 gm |

The ammonium chloride concentration was 16 mM (0.856 gm/liter) and supplied 90% of the total nitrogen with the remaining 10% supplied from yeast extract and sodium glutamate. The culture was operated at a dilution rate of 0.09 hr⁻¹ for 268 hours and yielded an average cell concentration of 2.09 gm/liter, with an average specific productivity of 0.125 gm/gm cells/hr. Over the next 91 hours, the nitrogen concentration in the medium was gradually increased by addition of supplemental nitrogen in the form of ammonia gas. When steady state was reached, the culture operated for 244 hrs. at a cell concentration of 4.23 gm/liter (average), and the specific productivity increased to an average value of 0.17 with a range of 0.16 to 0.2 gm xanthan/gm cells/hr.

Thus, it is seen that in the above examples, specific productivity was increased by increasing cell concentration through the use of supplemental ammonium ion provided from ammonia gas. The data obtained in Example II are reproduced in the table below:

TABLE II

| Time Period (Hour) | Cell Conc'n (gm/liter) | Xanthan (conc'n %) | Visc. (cp) | Xanthan Spec. Prod. (gm/gm cells/hr) | Dilution Rate (hr⁻¹) |
|---|---|---|---|---|---|
| 48–316 | 2.09 | 0.32 | 600 | 0.125 | 0.09 |
| 316–407 | Incrementally increase N in feed using NH₃ | | | | |
| 407–651 | 4.23 | 0.80 | 1580 | 0.17 | 0.09 |

From the foregoing description, it will be apparent that the present invention provides a means for substantially improving the efficiency (specific productivity) of bacteria of the genus Xanthomonas to produce xanthan gum. This development has a very practical application in plants for the commercial production of xanthan.

I claim:

1. In a continuous process for the production of a heteropolysaccharide by continuously culturing a microorganism of the genus Xanthomonas in a nutrient medium being added to a fermentation zone, withdrawing a heteropolysaccharide-containing effluent from said zone while continuing said process at a rate such that an essentially steady state condition is maintained, the improvement which comprises conducting said process (1) in the presence of sufficient growth limiting nutrient in said medium to produce an average cell concentration of said microorganism of from about 1.5 to less than about 3 gm/liter, and (2) thereafter increasing the growth limiting nutrient in said medium to produce an increased cell concentration of said microorganism of not more than about 5 gm/liter whereby the quantity of said heteropolysaccharide produced per gram of said microorganism at steady state condition is increased.

2. The process of claim 1 in which nitrogen is employed as the limiting growth nutrient in said medium.

3. The process of claim 2 in which the growth limiting nutrient in said medium is held at a concentration level of from about 0.001 to about 0.07 percent.

4. The process of claim 2 in which the limiting growth nutrient in said medium ranges from about 0.1 to 15 percent of the desired microorganism concentration.

5. The process of claim 1 in which the average concentration of said microorganism produced in said medium in step (2) ranges from about 3 to about 5 grams/liter.

6. The process of claim 1 wherein said medium contains essentially glucose, mineral salts, $NH_4Cl$, and a mixture of vitamins.

7. The process of claim 1 in which the heteropolysaccharide is xanthan.

8. The process of claim 2 in which the nitrogen as the growth limiting nutrient is supplied by glutamic acid.

9. The process of claim 2 in which the growth limiting nutrient is nitrogen supplied by one of the group consisting of ammonium chloride and ammonia gas.

10. The process of claim 2 in which the growth limiting nutrient is nitrogen which is supplied by yeast extract.

11. The process of claim 4 in which the limiting growth nutrient in said medium ranges from about 8 to about 10 percent of the desired microorganism concentration.

12. The process of claim 6 in which the glutamic acid is added to said medium.

13. The process of claim 12 in which yeast extract is added to said medium.

14. The process of claim 1 which comprises additionally conducting step (1) for at least about three culture turnovers.

15. The process of claim 14 wherein step (1) is conducted for at least about ten culture turnovers.

16. The process of claim 1 in which the initial average cell concentration is about 1.5 gm to about 2.5 gm/liter.

* * * * *